(12) United States Patent
Mosnier et al.

(10) Patent No.: US 9,987,048 B2
(45) Date of Patent: Jun. 5, 2018

(54) VERTEBRAL OSTEOSYNTHESIS EQUIPMENT ENABLING ILIAC ANCHORING OF A VERTEBRAL BAR

(71) Applicant: MEDICREA INTERNATIONAL, Rillieux la Pape (FR)

(72) Inventors: Thomas Mosnier, Anthon (FR); Frank Schwab, New York, NY (US)

(73) Assignee: MEDICREA INTERNATIONAL, Rillieux la Pape (FR)

( * ) Notice: Subject to any disclaimer, the term of this patent is extended or adjusted under 35 U.S.C. 154(b) by 0 days. days.

(21) Appl. No.: 15/302,491

(22) PCT Filed: Apr. 10, 2015

(86) PCT No.: PCT/IB2015/052629
§ 371 (c)(1),
(2) Date: Oct. 7, 2016

(87) PCT Pub. No.: WO2015/159194
PCT Pub. Date: Oct. 22, 2015

(65) Prior Publication Data
US 2017/0020578 A1    Jan. 26, 2017

(30) Foreign Application Priority Data
Apr. 17, 2014  (FR) ...................... 14 53465

(51) Int. Cl.
*A61B 17/70*  (2006.01)
(52) U.S. Cl.
CPC ...... *A61B 17/7055* (2013.01); *A61B 17/7041* (2013.01)
(58) Field of Classification Search
CPC ................ A61B 17/7055; A61B 17/7041
(Continued)

(56) References Cited

U.S. PATENT DOCUMENTS 5,474,551 A   12/1995  Finn et al.
5,549,607 A    8/1996  Olson
(Continued)

FOREIGN PATENT DOCUMENTS

FR    2956803 A1    9/2011

OTHER PUBLICATIONS

Search Report of the French Patent Authority Dec. 22, 2014.

*Primary Examiner* — Pedro Philogene
*Assistant Examiner* — David C Comstock
(74) *Attorney, Agent, or Firm* — PatShegan IP

(57) ABSTRACT

This equipment comprises an iliac rod (2), a connection assembly (3, 4) for connecting that iliac rod to a vertebral bar, an iliac anchoring member and an iliac part connecting the iliac rod to that iliac anchoring member; said connecting assembly (3, 4) is independent of the iliac rod (2) and comprises two portions, namely: —a first portion (3), for connecting to said vertebral bar (50), that forms a closed conduit (10) for engagement of that portion (3) on that bar (50); and —a second portion (4), for connecting to said iliac rod (2), that forms a conduit (12) for the engagement of that second portion (4) on the iliac rod (2). According to the invention, —said first portion is formed by a first connecting part (3) and said second portion is formed by a second connecting part (4), said first and second connecting parts (3, 4) being independent of one another; said first connecting part (3) comprises a portion (3a) that forms said closed conduit (10) and a threaded rod (3b) protruding from said portion (3a); said second connecting part (4) forms a passage (11) through it for the engagement of said threaded rod (3b) of the first connecting part (3), with a pivoting capacity of said second connecting part (4) relative to said first connecting part (3).

4 Claims, 2 Drawing Sheets

(58) Field of Classification Search
USPC ....... 606/246, 250, 253, 264–267, 269, 272, 606/277, 278, 305, 308, 310, 324
See application file for complete search history.

(56) References Cited

U.S. PATENT DOCUMENTS

| | | | |
|---|---|---|---|
| 5,947,965 A | 9/1999 | Bryan | |
| 2006/0241601 A1* | 10/2006 | Trautwein | A61B 17/7049 606/248 |
| 2008/0021454 A1* | 1/2008 | Chao | A61B 17/7044 606/250 |

\* cited by examiner

VERTEBRAL OSTEOSYNTHESIS EQUIPMENT ENABLING ILIAC ANCHORING OF A VERTEBRAL BAR

The present invention relates to vertebral osteosynthesis equipment allowing iliac anchoring of a vertebral bar.

Vertebral osteosynthesis equipment comprises, in a manner well known in itself:
- at least one so-called "vertebral" rigid bar, designed to extend along several vertebrae, and generally two bars designed to be placed on either side of the processes of the vertebrae;
- bone anchoring members, such as pedicular screws or laminar hooks, designed to anchor the bar(s) to the vertebrae to be immobilized;
- connecting parts making it possible to connect the bar(s) to the bone anchoring members; and
- mounting means making it possible to mount the connecting parts on the bone anchoring members and to immobilize those parts relative to those members.

Known equipment of this type is in particular described by patent application publication No. WO 98/55038. In this equipment, each bone anchoring member is of the so-called "polyaxial" type, i.e., it comprises a threaded proximal pin articulated relative to a threaded base designed to be screwed into a vertebral pedicle; each connecting part comprises a passage allowing it to be engaged on that threaded proximal pin, and each mounting means is made up of a nut designed to be screwed on said threaded proximal pin.

In the frequent case where vertebral osteosynthesis is done for the lumbar vertebrae, it is necessary to anchor the lower end of a vertebral bar, or of two vertebral bars, comprised by the equipment serving for the vertebral osteosynthesis, to the iliac portion(s) of the patient's pelvis.

In order to perform such iliac anchoring, it is known to use (i) an iliac rod secured to a connecting portion forming a closed conduit for engaging on the vertebral bar, i.e., a conduit completely surrounding the bar when said connecting portion is engaged on the bar, and (ii) an iliac anchoring screw receiving a connecting piece making it possible to connect the iliac rod to that screw. The iliac anchoring screw is in particular of the aforementioned "polyaxial" type.

Such equipment is not particularly satisfactory in practice, because its placement involves significant mobilization of the muscles and other surrounding tissue when it is necessary to perform both the axial engagement of said connecting portion on the vertebral bar and the engagement of the iliac rod in the connecting piece engaged on the iliac anchoring screw.

To resolve this problem, it has been considered to make said connecting portion in an "open" manner, i.e., with a clamp structure allowing engagement that is no longer axial on the vertebral bar, but transverse.

The placement of this type of equipment involves less significant mobilization of the muscles and other tissue than the first aforementioned type of equipment, but has the drawback of presenting uncertain resistance to the repeated forces exerted by the patient's movements.

U.S. Pat. No. 5,474,551 describes vertebral osteosynthesis equipment making it possible to perform iliac anchoring of the vertebral bar, comprising an iliac rod, a part connecting that iliac rod to a vertebral bar, an iliac anchoring member and an iliac part connecting the iliac rod to that iliac anchoring member;
said connecting part is independent of the iliac rod and comprises two portions secured to one another, namely:
- a first portion, for connecting to said vertebral bar, that forms a closed conduit for engagement of that portion on that bar, i.e., a conduit completely surrounding the bar when that first connecting portion is engaged on the bar; said conduit is dimensioned to allow an adjusted engagement of said first connecting portion on the bar, but with a pivoting capacity of that portion relative to that bar; and
- a second portion, for connecting to said iliac rod, that forms a conduit for the engagement of that second portion on the iliac rod.

This equipment does not make it possible to resolve the aforementioned drawbacks of the existing equipment in a satisfactory manner.

The present invention therefore aims to resolve these drawbacks, and therefore to provide vertebral osteosynthesis equipment that has both a high resistance to the repeated forces exerted by the patient's movements and the placement of which involves reduced mobilization of the muscles and other surrounding tissues.

The equipment in question comprises, in a known manner, an iliac rod, a connection assembly connecting that iliac rod to a vertebral bar, an iliac anchoring member and an iliac part connecting that iliac rod to said iliac anchoring member;
said connection assembly is independent of the iliac rod and comprises two portions, namely:
- a first portion, for connecting to said vertebral bar, that forms a closed conduit for engagement of that portion on that bar, i.e., a conduit completely surrounding the bar when that first connecting portion is engaged on the bar; said conduit is dimensioned to allow an adjusted engagement of said first connecting portion on the bar, but with a pivoting capacity of that portion relative to that bar; and
- a second portion, for connecting to said iliac rod, that forms a conduit for the engagement of that second portion on that iliac rod.

According to the invention,
said first portion is formed by a first connecting part and said second portion is formed by a second connecting part, said first and second connecting parts being independent of one another;
said first connecting part comprises a portion that forms said closed conduit and a threaded rod protruding from said portion;
said second connecting part forms a passage through it for the engagement of said threaded rod of the first connecting part, with a pivoting capacity of said second connecting part relative to said first connecting part; and
the equipment comprises a nut able to be screwed on said threaded rod so as to assemble said second connecting part to said first connecting part and, when it is tightened, to immobilize those two connecting parts relative to one another.

Thus, in practice, said first connecting part, assembled without tightening to said second connecting part, is axially engaged on the vertebral bar, and said iliac connecting part is placed on the iliac bone anchoring member, previously implanted; the iliac rod is next engaged in the conduits formed by said second connecting part and said iliac connecting part, then the nut is tightened so as to immobilize the two connecting parts relative to one another. The possibility of pivoting of these two connecting parts relative to one another before tightening of the nut, and the possibility of pivoting of the same parts with the vertebral bar and the iliac rod, respectively, allows placement of the equipment according to the invention with reduced mobilization of the muscles and other surrounding tissue. The fact that the first connecting part forms a closed conduit for engagement on the vertebral bar and the two connecting parts are perfectly connected to one another by a screwed connection simultaneously makes it possible to obtain an assembly clearly able to withstand the repeated forces resulting from the patient's movements.

Preferably, the second connecting part comprises two parallel branches and a curved intermediate section, those two parallel branches and that curved section jointly forming said engagement conduit of the iliac rod, which is a quasi-closed engagement conduit, i.e., surrounding the iliac rod over most of the circumference of that rod; said parallel branches are pierced with coaxial holes constituting said engagement passage of the threaded rod.

This part structure makes it possible, during tightening of the nut, to bring said parallel branches closer together and, in so doing, to close said curved intermediate section around the iliac rod. Complete immobilization of that rod relative to the second connecting part is thus obtained.

Preferably, said iliac connecting part has a structure with two parallel branches and curved intermediate section, identical to that of said second connecting part; the passage formed by the coaxial holes arranged in parallel branches then receives a threaded proximal pin comprised by the iliac anchoring member.

Complete immobilization of the iliac rod relative to that iliac connecting part is also obtained.

Preferably, at least one among said first connecting part and said second connecting part has an irregular and rough surface, in particular knurled, at the face designed to come into contact with the other part.

A complete immobilization of one part relative to the other is thus obtained when said nut is tightened.

The invention will be well understood, and other features and advantages thereof will appear, using the following description, done in reference to the appended diagrammatic drawing; this drawing shows, as a non-limiting example, one preferred embodiment of the equipment in question.

Figure 1:
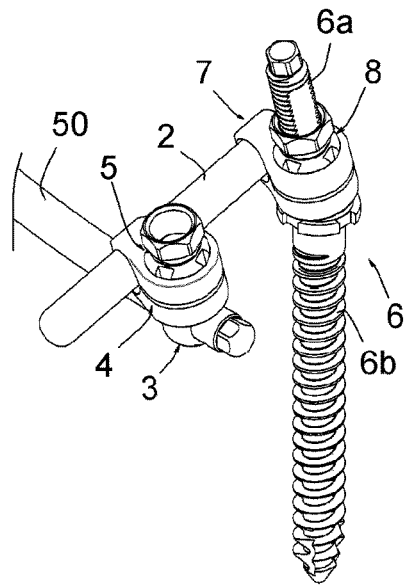
FIG. 1 is a perspective view of this equipment, in the completely assembled state, in which this equipment makes it possible to perform the iliac anchoring of a vertebral bar.
Figure 2:
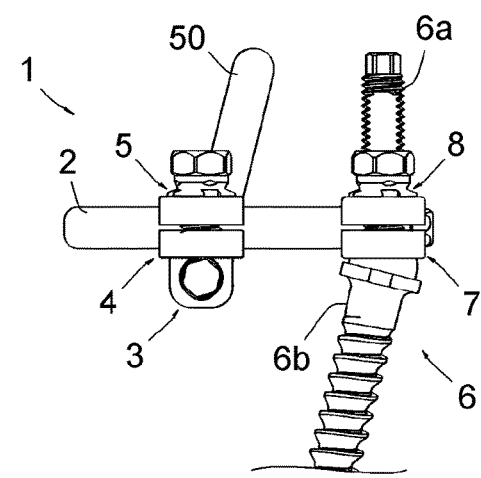
FIG. 2 is a side view thereof.
Figure 3:
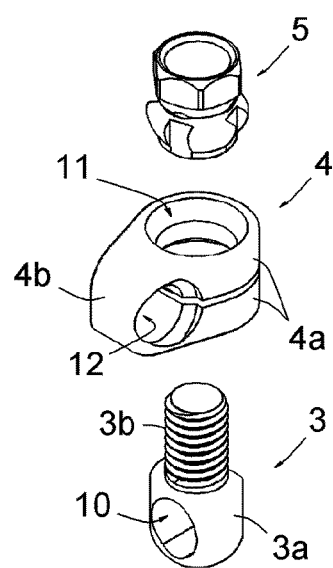
FIG. 3 is an exploded an enlarged perspective view of a first and second connecting part comprised by this equipment, and a nut making it possible to assemble these two connecting parts to one another.
Figure 4:
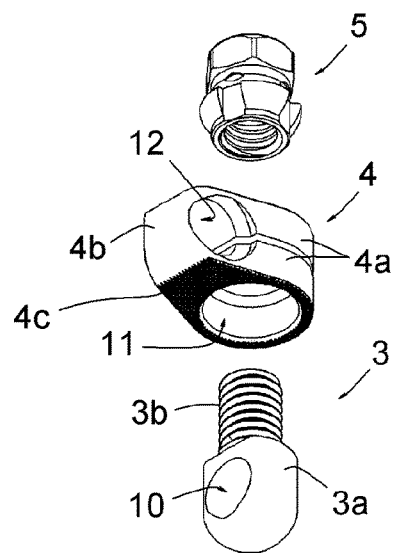
FIG. 4 is a view of those same parts similar to FIG. 3, in perspective view from another angle.

FIGS. 1 and 2 show vertebral osteosynthesis equipment 1 allowing the iliac anchoring of a vertebral bar 50. This vertebral bar 50 is a rigid bar designed to extend along several vertebrae and that is anchored to the latter using bone anchoring members, such as pedicular screws or laminar hooks, the bar 50 being connected to those bone anchoring members by connecting parts, which in turn are connected to the bone anchoring members by connecting members such as nuts. This bar 50, these bone anchoring members, these connecting parts and these nuts can in particular be according to those described by patent application publication No. WO 98/55038.

This equipment 1 comprises an iliac rod 2, an assembly 3, 4, 5 for connecting the iliac rod 2 to the vertebral bar 50, an iliac anchoring polyaxial screw 6, an iliac part 7 for connecting the iliac rod 2 to that screw 6, and a nut 8 for mounting the part 7 on the screw 6.

The iliac rod 2 is a rigid rod, in particular with a diameter of 5 to 6 mm and a length sufficient to connect the screw 6 implanted in the iliac portion of a patient's pelvis, to the bar 50. This length is for example from 30 to 50 mm.

The connection assembly 3, 4, 5 comprises a first connecting part 3, a second connecting part 4 and a nut 5.

The first connecting part 3 allows the connection of said assembly to the vertebral bar 50. It comprises a portion 3a forming a conduit 10 for the engagement on that bar 50, and a threaded rod 3b secured to that portion 3a. The conduit 10 is closed, i.e., it completely surrounds the bar 50 when the part 3 is engaged on that bar, and is dimensioned to allow an adjusted engagement of the part 3 on that bar, but with a pivoting capacity of the part 3 relative to that bar.

The second connecting part 4 allows a connection of said assembly to the iliac rod 2. It comprises two parallel branches 4a and a curved intermediate portion 4b. The branches 4a are pierced with two coaxial holes constituting a passage 11 for engagement of the threaded rod 3a, the passage and that rod being dimensioned such that said engagement is done with a pivoting capacity of the part 4 relative to the part 3. The branches 4a, jointly with the portion 4b, form a conduit 12 for engagement of the iliac rod 2. This conduit 12 is quasi-closed, i.e., it surrounds the rod 2 over most of the circumference of that rod. The curved intermediate section 4b is slightly flexible so as to allow a normal position of the branches 4a, in which those branches 2a are separated from each other and allow the rod 2 to be engaged in the conduit 12, and a close position of the branches 4a, in which that curved intermediate portion 4b and those branches 4a grip the rod 2 between them.

The part 4 also has an irregular and rough surface 4c, in particular knurled, at its base designed to come into contact with the part 3.

The nut 5 is of the traditional type in this application. Because it is well known in itself, it will not be described in any particular detail. It is able to be screwed on the rod 3b so as to tighten the part 3 against the part 4 and simultaneously bring the branches 4a closer to one another.

The screw 6 is, in the illustrated example, of the "polyaxial" type, i.e., comprising a threaded proximal pin 6a articulated relative to a threaded base 6b designed to be screwed in the iliac portion of the pelvis. This screw may in particular be of the type described in patent application publication No. WO 98/55038.

The connecting part 7 has a same structure as the part 4. The coaxial holes arranged in its parallel branches form a passage allowing it to be engaged on the threaded proximal pin 6a.

The nut 8 is designed to be screwed on the pin 6a. It has the same structure as the nut 5.

Figure 5:
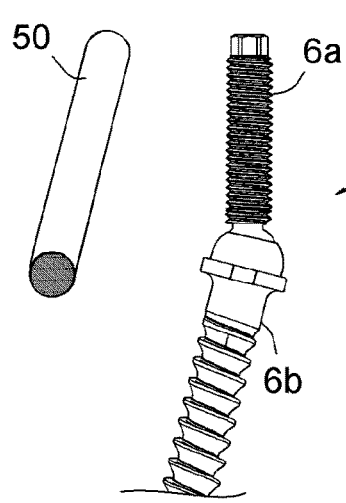
FIGS. 5 to 7 are views of different parts of the equipment, from the side and in section, during three successive steps for placement of this equipment.
Figure 6:
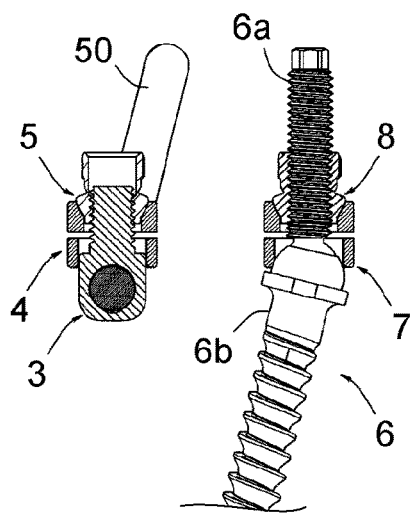
Figure 7:
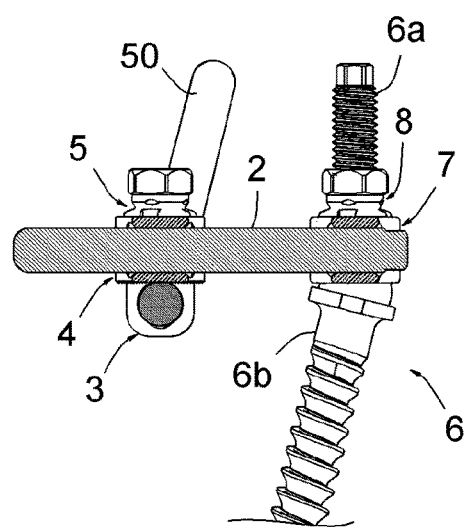

In practice, as shown in FIGS. 5 to 7, the screw 6 is placed in the iliac portion of the patient's pelvis (cf. FIG. 5), then the part 3, assembled to the part 4 using the nut 5, without tightening of the latter, is axially engaged on the vertebral bar 50; the iliac connecting part 6 is engaged on the pin 6a of the screw 6, then the nut 8 is screwed on that pin, without tightening (cf. FIG. 6); the iliac rod 2 is next engaged in the conduits formed by part 4 and the part 7, then the nuts 5 and 8 are tightened so as to immobilize the two parts 3, 4 relative to one another and immobilize the rod 2 relative to the parts 4 and 7 (cf. FIG. 7).

During this assembly, the possibility of pivoting of the parts 3 and 4 relative to one another before tightening of the nut 5, and the possibility of pivoting of those same parts with the vertebral bar 50 and the iliac rod 2, respectively, allows placement of the equipment 1 with a reduced mobilization of the muscles and other surrounding tissue. The fact that the part 3 forms a closed engagement conduit on the vertebral bar 50 and that the two connecting parts are perfectly connected to one another by a screwed connection simultaneously allows the equipment to be clearly able to withstand the repeated forces resulting from the patient's movements.

This vertebral osteosynthesis equipment 1 consequently has a decisive advantage relative to the existing counterpart equipment.

The invention has been described above in reference to one embodiment provided as an example. It is of course not limited to that embodiment, but extends to all other embodiments covered by the appended claims.

The invention claimed is:

1. Vertebral osteosynthesis equipment enabling iliac anchoring of a vertebral bar, comprising:
    an iliac rod,
    a connecting assembly for connecting the iliac rod to a vertebral bar;
    an iliac anchoring member; and
    an iliac connector for connecting the iliac rod to the iliac anchoring member;
    wherein said connecting assembly is independent of the iliac rod and comprises a first connecting portion for connecting to the vertebral bar, and a second connecting portion, independent of the first connecting portion, for connecting to said iliac rod;
        and wherein the first connecting portion, includes a closed conduit for engagement of a section of the vertebral bar, such that the conduit completely surrounds the section when the conduit is engaged on the vertebral bar; said conduit is dimensioned to allow an adjusted engagement of said first connecting portion on the vertebral bar, and is configured to allow pivoting of the first portion relative to the vertebral bar; and
        and wherein the second connecting portion, includes a conduit for engagement on the iliac rod
    and wherein said first connecting portion further includes a protruding threaded rod; and said second connecting portion includes a passage for the engagement of said protruding threaded rod configured to allow pivoting of said second connecting portion relative to said first connecting portion;
    and wherein the connecting assembly includes a nut configured to be screwed on said protruding threaded rod so as to assemble said second connecting portion to said first connecting portion such that when said nut is tightened to said protruding threaded rod, the first and second connecting portions are immobilized relative to one another.

2. Equipment according to claim 1, wherein the second connecting portion comprises two parallel branches and a curved intermediate section, wherein the two parallel branches and the curved section jointly forming said engagement conduit of the iliac rod, which is a quasi-closed engagement conduit, i.e., surrounding the iliac rod over most of the circumference of that rod; said parallel branches are pierced with coaxial holes constituting said engagement passage of the threaded rod.

3. Equipment according to claim 2, wherein said iliac connector has a structure with two parallel branches and curved intermediate section, identical to that of said second connecting portion; the passage formed by the coaxial holes arranged in parallel branches then receives a threaded proximal pin comprised by the iliac anchoring member.

4. Equipment according to claim 1, wherein at least one among said first connecting portion and said second connecting portion has an irregular and rough surface, in particular knurled, at the face designed to come into contact with the other part.

\* \* \* \* \*